(12) United States Patent  (10) Patent No.: US 8,410,434 B1
Moskovets et al.  (45) Date of Patent: Apr. 2, 2013

(54) THERMO-STABILIZED NANO- AND MICRO-FLOW LC/ESI-MS INTERFACE AND A METHOD THEREOF

(75) Inventors: Eugene Moskovets, Columbia, MD (US); Alexander R. Ivanov, Brighton, MA (US); Vladimir Doroshenko, Sykesville, MD (US)

(73) Assignee: Science & Engineering Services, Inc., Columbia, MD (US)

( * ) Notice: Subject to any disclaimer, the term of this patent is extended or adjusted under 35 U.S.C. 154(b) by 33 days.

(21) Appl. No.: 13/235,033
(22) Filed: Sep. 16, 2011
(51) Int. Cl.
 *H01J 49/10* (2006.01)
(52) U.S. Cl. .................................................... 250/288
(58) Field of Classification Search .............. 250/288
 See application file for complete search history.

(56) References Cited

U.S. PATENT DOCUMENTS 7,547,555 B2 * 6/2009 Sheehan ....................... 436/173

* cited by examiner

*Primary Examiner* — Kiet T Nguyen
(74) *Attorney, Agent, or Firm* — Oblon, Spivak, McClelland, Maier & Neustadt, L.L.P.

(57) ABSTRACT

A liquid chromatography interface is provided having an integrated column/ESI tip assembly including a liquid chromatography separation column, an ESI tip for generating ions having at least one emitting channel, and a temperature-controlled enclosure surrounding the liquid chromatography separation column. The enclosure has at least one opening and the ESI tip is exposed outside the enclosure through the opening. The enclosure has a heating or cooling device providing a substantially homogeneous distribution of temperature throughout an internal space of the enclosure where the liquid chromatography separation column is disposed. The enclosure includes at least one gas flow mixing element to permit heat exchange by directing a flow of gas toward the ESI tip. The integrated column/ESI tip assembly resides within a thermo-stabilized volume of substantially the same temperature from an entrance of the liquid chromatography separation column to the outlet of the ESI tip.

35 Claims, 9 Drawing Sheets

THERMO-STABILIZED NANO- AND MICRO-FLOW LC/ESI-MS INTERFACE AND A METHOD THEREOF

BACKGROUND OF THE INVENTION

1. Field of the Invention

This invention is related to interfacing liquid chromatography to mass spectrometry. More specifically it is related to interfacing liquid nano- and micro-capillary chromatography to mass spectrometry using electrospray ionization.

2. Description of the Related Art

It is well recognized that conducting liquid chromatography (LC) at elevated temperatures (typically 30-80° C.) results in beneficial effects, such as improvements in peak shape, selectivity, retention time stability, chromatographic resolution, and speed of analysis. [Snyder, L. R.; Kirkland, J. J.; Glajch, J. L. Practical HPLC Method Development, 2nd ed.; Wiley & Sons: New York, 1997; Dolan, J. W. J. Chromatogr., A 2002, 965 (1-2), 195-205.5,6]. Temperature affects several physical parameters in liquid chromatography such as retention factor of analytes, analyte diffusion, and mobile phase viscosity.

High Performance Liquid Chromatographic (HPLC) or Ultra Performance Liquid Chromatography (UPLC) separations performed in capillary as well as in large-scale HPLC columns those with the internal diameter (i.d.) larger than 0.5 mm, at elevated temperatures have also other advantages such as reducing carryover, lowering column pressure, and increasing speed of the analysis [Rosés M, Subirats X, Bosch E., J. Chromatogr A. 2009 Mar. 6; 1216(10):1756-75].

The use of mass spectrometry (MS) as a detector of compounds separated by LC substantially increased the applicability of the chromatography as an analytical method. Typically, an electrospray ionization (ESI) technique is used to ionize the analyte molecules containing in the eluent before directing the analyte ions to mass spectrometer (MS) or ion mobility spectrometer (IMS) for chemical analysis. In electrospray, the liquid sample is sprayed using a silica or metal capillary (an ESI tip) by the action of high voltage applied to the tip, column, HPLC eluent, or liquid sample to be sprayed. After generation, the charged liquid micro-droplets start to evaporate. The analyte ions are formed from charged microdroplets in a process of solvent evaporation that is accompanied by a multiple droplet division due to Coulomb repulsion of surface charges. After the droplet diameter shrinks to some critical size, the analyte ions are produced in the eventual process of field emission.

An integrated LC column typically has a silica capillary that is ended with an ESI tip made from the same silica capillary by pulling the capillary end at high temperature to make its internal and outer diameter smaller, although the ESI tip can be fabricated separately. This integrated column/ESI tip assembly is packed with chromatographic media starting from the open end of the column to its tip. (When the tip is a separate body made of narrow internal diameter fused silica, metal, glass and other materials, it is typically not packed.) The integrated column is connected via union to the supply capillary with a flow of a mobile phase from an HPLC pump. Mobile phases are typically mixtures of organic and aqueous solvents (e.g., water mixed with acetonitrile) with the flow rate typically in the range of 100-1000 nL/min. This so-called nano-flow regime gives the term of nano-LC for the columns operating at nL/min flow rates [Chen G, Pramanik BN, LC-MS for protein characterization: current capabilities and future trends. *Expert Rev Proteomics.* 2008; 5(3): 435-44.] Similarly, micro-capillary LC (or micro-LC) corresponds to the flow rates in the μL/min range. Such low flow rates typically require the use of ESI tips with narrow droplet emitting channels.

Compared to capillary and large-scale HPLC columns, operating integrated nano-LC/ESI at the elevated temperatures is not straightforward. As an example, the data for nano-LC column with a compact heater recently commercialized by Phoenix S&T (Chester, Pa., USA) indicate that the use of elevated temperatures broadens the LC peaks for individual peptides (they are up to 2 times wider at 50° C. compared to those at 20° C.).

The entire contents of the references listed above are incorporated herein in their entirety by reference.

SUMMARY OF THE INVENTION

In one embodiment of the invention, there is provided a liquid chromatography interface having an integrated column/ESI tip assembly including a liquid chromatography separation column, an ESI tip for generating ions having at least one emitting channel with an internal size less than or equal to 30 microns, a temperature-controlled enclosure surrounding the liquid chromatography separation column. The enclosure has at least one opening and the ESI tip is exposed outside the enclosure through the opening. The enclosure has a heating or cooling device providing a substantially homogeneous distribution of temperature throughout an internal space of the enclosure where the liquid chromatography separation column is disposed. The enclosure includes at least one gas flow mixing element to permit heat exchange by directing a flow of gas toward the ESI tip. The integrated column/ESI tip assembly resides within a thermo-stabilized volume of substantially the same temperature from an entrance of the liquid chromatography separation column to an end of the ESI tip.

In one embodiment, there is provided a liquid chromatography interface having an integrated column/ESI tip assembly including a liquid chromatography separation column, an ESI tip for generating ions, a temperature-controlled enclosure surrounding the liquid chromatography separation column. The enclosure has at least one opening and the ESI tip is exposed outside the enclosure through the opening. The enclosure has a heating or cooling device providing an enclosure temperature having a substantially homogeneous enclosure temperature distribution throughout an internal space of the enclosure where the liquid chromatography separation column is disposed. The enclosure holds liquid chromatography separation columns having different lengths. The integrated column/ESI tip assembly, including the liquid chromatography separation columns of an arbitrary length, resides within a thermo-stabilized volume of substantially the same temperature from an entrance of the liquid chromatography separation column to an end of the ESI tip.

In one embodiment of the invention, there is provided a method for separation of analytes in elution time in a liquid chromatography separation column. The method provides a thermo-stabilized volume of substantially the same temperature from the entrance of the liquid chromatography separation column to the outlet of an electrospray ionization (ESI) tip. The method transits a sample through the liquid chromatography separation column to an end of the ESI tip.

In one embodiment of the invention, there is provided a system for analyte characterization having an integrated column/ESI tip assembly including a liquid chromatography separation column, an ESI tip for generating ions, a temperature-controlled enclosure surrounding the liquid chromatography separation column, and a mechanism configured to characterize analyte eluting from the liquid chromatography separation column. The enclosure has at least one opening and the ESI tip is exposed outside the enclosure through the opening. The enclosure has a heating or cooling device providing a substantially homogeneous distribution of temperature throughout an internal space of the enclosure where the liquid chromatography separation column is disposed. The enclosure includes at least one gas flow mixing element to permit heat exchange by directing a flow of gas toward the ESI tip. The integrated column/ESI tip assembly resides within a thermo-stabilized volume of substantially the same temperature from an entrance of the liquid chromatography separation column to an end of the ESI tip.

In one embodiment of the invention, there is provided a system for analyte characterization having an integrated column/ESI tip assembly including a liquid chromatography separation column, an ESI tip for generating ions, a temperature-controlled enclosure surrounding the liquid chromatography separation column, and a mechanism configured to characterize analyte eluting from the liquid chromatography separation column. The enclosure has at least one opening and the ESI tip is exposed outside the enclosure through the opening. The enclosure has a heating or cooling device providing an enclosure temperature having a substantially homogeneous enclosure temperature distribution throughout an internal space of the enclosure where the liquid chromatography separation column is disposed. The enclosure holds liquid chromatography separation columns having different lengths. The integrated column/ESI tip assembly, including the liquid chromatography separation columns of an arbitrary length, resides within a thermo-stabilized volume of substantially the same temperature from an entrance of the liquid chromatography separation column to an end of the ESI tip.

In one embodiment of the invention, there is provided a method for separation of analytes in elution time in a liquid chromatography separation column. The method provides a thermo-stabilized volume having a substantially same instantaneous temperature from an entrance of the liquid chromatography separation column to an outlet of an electrospray ionization (ESI) tip. The method introduces the analytes into the liquid chromatography separation column in the thermo-stabilized volume. The method ramps the substantially same instantaneous temperature of the thermo-stabilized volume over a prescribed duration such that the instantaneous temperature is a controlled as a function of time, with no substantial variation of the instantaneous temperature along a length to the liquid chromatography separation column. The temperature ramp can be performed simultaneously or intermittently with a gradient LC ramp. The method elutes the analytes from the ESI tip over the prescribed duration.

It is to be understood that both the foregoing general description of the invention and the following detailed description are exemplary, but are not restrictive of the invention.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DETAILED DESCRIPTION OF THE INVENTION

This invention provides a way to run a nano-LC and micro-LC column at elevated temperatures with improved nano-LC/MS performance, including narrower peak widths of analytes at the elevated temperatures compared to those at the room temperature, including improvements in separation efficiency, and including better reproducibility in retention times and better ESI MS detection sensitivity. The inventors do not know any prior work addressing the problem of the temperature induced broadening of peaks specific to integrated nano-LC/ESI columns interfaced with the MS.

Some of the embodiments of the present invention relate to ways to keep a homogeneous temperature along an entire length integrated nano-LC columns interfaced with mass spectrometers. While illustrated below with nano-LC columns, the invention includes similar embodiments as described below for nano-LC columns but applied in micro-LC columns.

In one embodiment of this invention, a homogeneous temperature along the entire length of columns is provided and maintained (at the same elevated or cooled) temperature along both 1) the section of the integrated nano-LC column residing inside a thermally isolated enclosure and 2) the section of the integrated nano-LC column residing outside the boundaries of the enclosure and thereby placed near the inlet to the mass spectrometer and exposed to ambient elements.

In one embodiment of this invention, the homogeneous elevated temperature along the section of the column inside the enclosure is maintained using distributed heating elements as well as a forced air mixing. In one embodiment, the homogeneous elevated temperature along the section of the column outside the enclosure is maintained using heating of this section by a flow of heated gas with temperature equal or close to the temperature inside the enclosure.

In one embodiment, the section of the integrated nano-LC column residing inside a thermally isolated enclosure and the section of the integrated nano-LC column residing outside the boundaries of the enclosure constitute a thermo-stabilized interface to a mass spectrometer or ion mobility spectrometer with the thermo-stabilized interface operating at a controlled (heated or cooled) temperature.

In another embodiment, a separate heating or cooling system is used to control temperature of heated or cooled pre-column or guard column that is fluidly connected to the nano-LC column.

Because the tip of the integrated silica nano-LC/ESI capillary column operates as an ion source, it is necessary to place this ESI tip very close to the inlet of mass spectrometer. Typically, due to geometrical constrains, the tip of the integrated capillary column and 10-20 mm of column length is exposed to ambient air while the rest of the column can be placed into the temperature controlled enclosure. In prior systems, due to small thermal mass of the exposed end of the column with an integrated ESI tip (e.g., the tip length is about 1 cm and the emitting channel internal diameter is typically below 30 microns) Because this part of the integrated column is exposed to ambient air, its temperature can be substantially different from the heated nano-LC column inside the enclosure.

This difference in temperatures results in a temperature gradient along the integrated column/ESI tip. The inventors have found that this temperature gradient accounts for peak broadening, especially when elevated temperatures are used. With this knowledge, the inventors have developed ways, as described herein, to reduce, minimize, and (in some cases) eliminate inadvertent temperature gradients within the LC interface to the MS. Without the measures taken by the invention to maintain a thermostabilized interface, substantial temperature gradient are typically present in nano- and micro-flow rate LC-MS interfaces without temperature stabilization. The MS inlet is typically heated to 110-350° C. and this heated inlet heats the outlet region of the LC column and creates a temperature gradient resulting in compromised separation performance and irreproducibility. The temperature stabilization of this invention eliminates or greatly reduces these problems.

Accordingly, this invention achieves homogeneous heating not only of the nano-LC column (as in the prior systems) but also along the entire integrated nano-LC/ESI tip assembly. Various embodiments of this invention with solutions for uniform heating of the entire nano-LC/ESI tip assembly are described below.

In order to solve the aforementioned problem of maintaining a homogeneous temperature along the entire length of the integrated nano-LC/ESI column, this invention in one embodiment provides a liquid chromatography/mass spectrometry system having a liquid chromatography separation capillary column placed into a thermo-stabilized enclosure, where the column ends with the integrated ESI tip.

Figure 1:
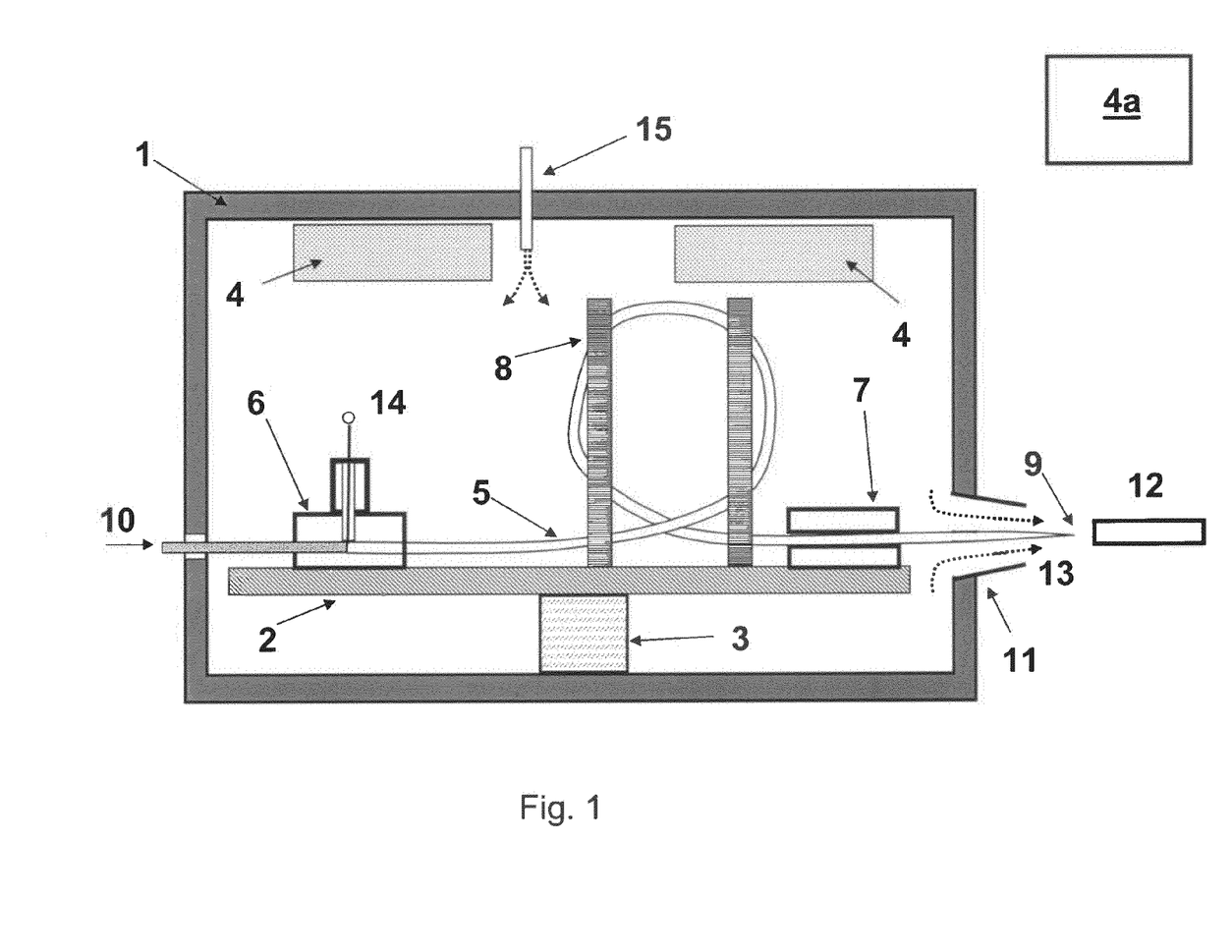
FIG. 1 is a schematic drawing of a nano-LC column placed inside a heated enclosure.

Referring now to the drawings where the same numbers in the different embodiments refer to similar or the same components, FIG. 1 is a schematic drawing of a nano-LC column 5 placed inside a heated enclosure 1. Also shown is a heater assembly 4 heating the exposed section of the column 5 including the ESI tip 9 by blowing the air heated inside the enclosure toward the ESI tip 9 and through the enclosure opening 11. The ESI tip can be produced at the end of the column by pulling of the glass or fused silica column end at a high temperature. Adjustment of a position of the ESI tip with respect to opening in enclosure 1 is provided by mechanical element 7. Positioning of the ESI tip 9 outside the enclosure 1 serves for the unobstructed delivering of electrosprayed liquid from the ESI tip 9 to a mass spectrometer (or ion mobility spectrometer) 12. The ESI tip can be positioned coaxially or at some angle relatively an inlet of mass spectrometer 12. Processor 4a provides a way to set and control the heating elements in enclosure 1 and thereby control the overall temperature of the enclosure and the elements therein as well as an instantaneous temperature during a temperature ramp or adjustment.

In one embodiment, to prevent influence of enclosure walls on the distribution of the electric field near the ESI tip, the ESI tip is placed at a distance of a few mm or more outside the enclosure. In one embodiment, the ESI tip is placed at a distance of 0.5 to 20 mm from the enclosure. Thermo-stabilized conditions in the enclosure 1 are provided by the heater assembly 4 that heats the gas in the enclosure 1 and that has a temperature control. The heater assembly 4 provides an almost homogenous temperature distribution in a volume of the enclosure that accommodates a major part of the integrated column 5. In one embodiment, the entire integrated nanoLC/ESI tip assembly that, due to its coiling (supported by brackets 8) can be of different length (from several centimeters to several meters long), can be kept at one and the same elevated temperature. In one embodiment, a section of the HPLC capillary 10 delivering liquid flow into the nanoLC column is held by a union, micro-tee, or micro-cross 6. Union made of conductive material or micro-tee (micro-cross) equipped with electrical contact 14 provide electrical current to liquid inside the nanoLC column from external electrical power supply. A section of the integrated nanoLC column 5 is inserted into the union (microTee) 6.

In one embodiment, ESI tip 9 has an emitting channel internal diameter with an internal size less than or equal to 30 microns. In one embodiment, ESI tip 9 has an emitting channel internal diameter with an internal size of 5 to 25 microns. In one embodiment, ESI tip 9 has an emitting channel internal diameter with an internal size of 10 to 20 microns. In one embodiment, ESI tip 9 has an emitting channel internal diameter with an internal size of 15 to 20 microns.

Thermo-stabilized conditions in the enclosure 1 are provided by the assembly 4 that heats the gas in the enclosure 1 and that has a temperature control. The assembly 4 provides an almost homogenous temperature distribution in a volume of the enclosure that accommodates a major part of the integrated column 5. In one embodiment, the entire integrated nano-LC/ESI tip assembly that, due to its coiling (supported by brackets 8) can be of different length (from several centimeters to several meters long), can be kept at one and the same temperature. In one embodiment, a section of the HPLC capillary delivering liquid flow into the nano-LC column is held by a union tee 6 (or micro-Tee). A section of the nano-LC column 5 is inserted into the union tee 6. These sections and the brackets 8 and adjusting system 7 are mounted on a base 2 which is separated from the walls of enclosure 1 by spacer 3. In this manner, these diverse components are kept at the same elevated or reduced temperature. Enclosure 1 can be placed onto a XYZ stage that controls the position of the ESI tip relative to the entrance to mass (ion mobility) analyzer 12.

In one embodiment of the invention, there is provided a way to maintain a generally stable temperature for the part of the integrated column that is exposed to ambient air. In this embodiment, the heated air from the enclosure 1 is blown out through the opening 11 toward the ESI tip using a separate gas supply subsystem (not shown). Make-up air is provided into the enclosure through inlet 15, introducing air into the enclosure nearly heating assembly 4 to minimize inadvertent cooling. A nozzle 11 surrounds a part of the ESI tip 9 and constrains the heated air 13 to thereby heat the tip 9 to the temperature close to that inside the enclosure.

Figure 2:
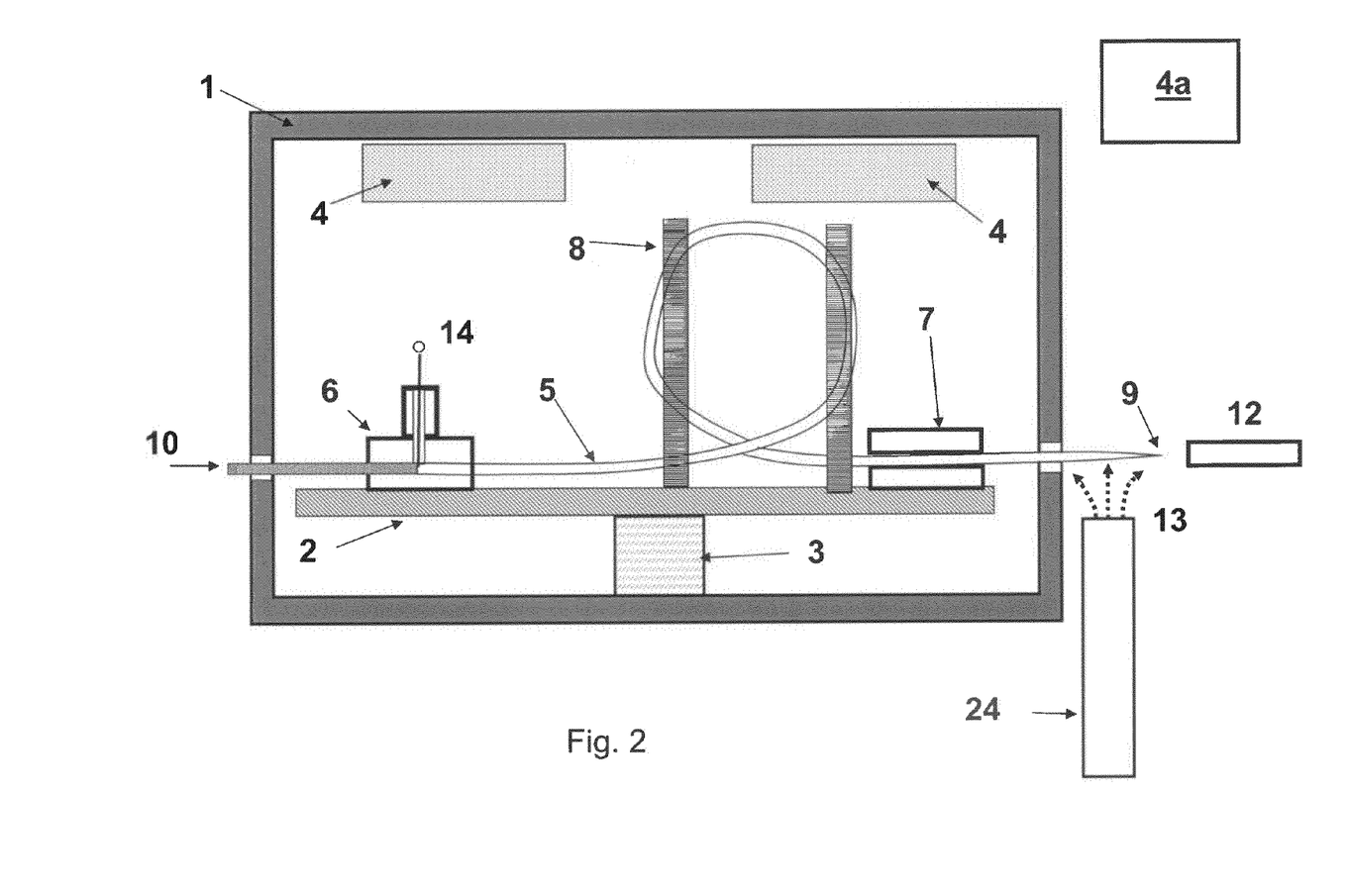
FIG. 2 is a schematic drawing of a nano-LC column placed inside a heated enclosure with a separate heater to provide a supplemental flow of heated air toward the ESI tip.

In another embodiment, a separate tubing or tubing assembly (as shown in FIG. 2) can provide a heated gas flow 13 to stabilize temperature in the region that includes the exposed part of the column 5. More specifically, FIG. 2 is a schematic drawing of a nano-LC column 5 placed inside enclosure 1 with a separate heater 24 that provides supplemental flow 13 of heated air toward the ESI tip 9. A temperature sensor (not shown) can measure the temperature of the exposed part of the ESI tip 9 or the gas stream (or sheath gas) near the exposed part.

In one embodiment, the heated gas stream (or sheath gas) can be supplemented or replaced with the flow of heated sheath liquids for LC, capillary electrophoresis (CE), capillary electrochromatogaphy (CEC), capillary isoelectric focusing (cIEF), capillary chromatofocusing (CCF), eluent desalting, buffer exchange, and other liquid phase-based applications coupled to mass spectrometry, where sheath liquids have been used. Sheath liquids are comprised of makeup solvents not interfering with or improving the ionization efficiency of analytes.

Figure 3:
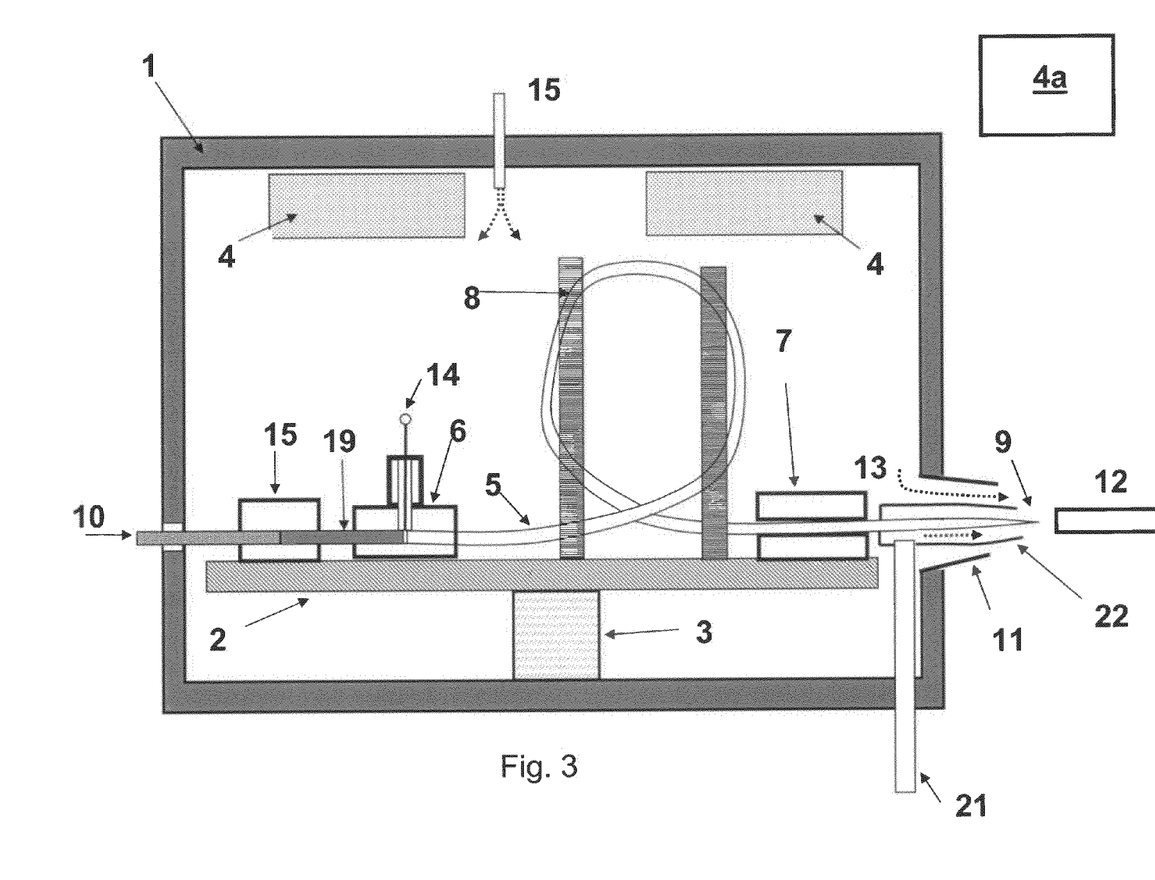
FIG. 3 is a schematic drawing of a nano-LC column placed inside a heated enclosure with the exposed section of the column with the ESI tip heated by way of a coaxial capillary surrounding the ESI tip.

More specifically, FIG. 3 is a schematic drawing of a nano-LC column 5 placed inside enclosure 1 with a separate heating assembly 22 placed near orifice 11 that provides a supplemental flow 13 of air or liquid toward the ESI tip 9 and is generally coaxial with distal part of the integrated column. The distal part of the column with ESI tip is placed inside a micro-tee or other type of union to provide a tight connection of integrated capillary 5 and heating assembly 22. Heating assembly 22 can be shaped as a tubing with internal diameter larger compared to external diameter of integrated capillary 5. The gap between heating assembly and the integrated column is filled with gas or sheath liquid supplied by means of tube 21. The temperature of a gas or sheath liquid is adjusted to that of integrated capillary 5 in enclosure 1.

Figure 4:
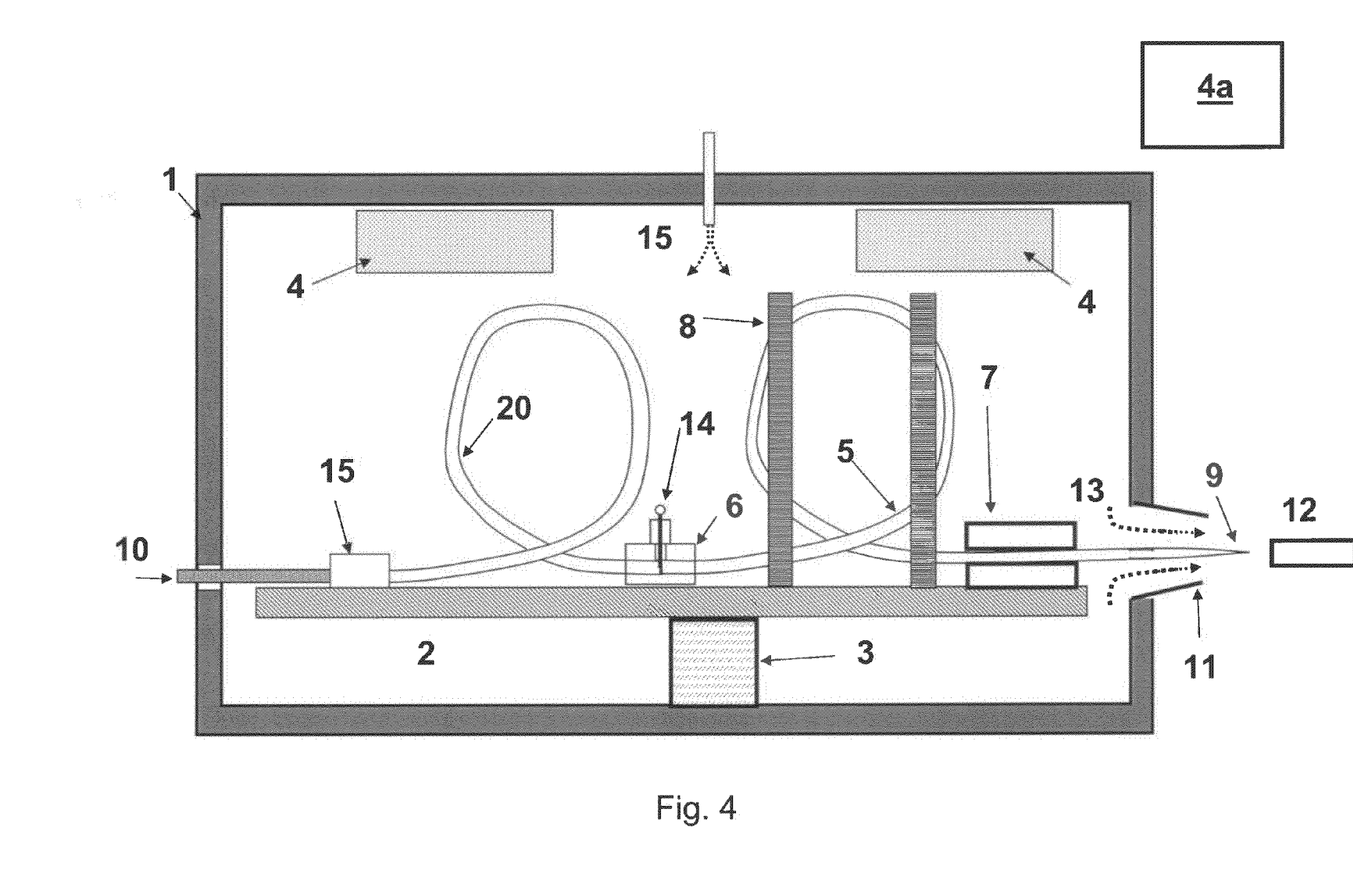
FIG. 4 is a schematic drawing of a first and second LC columns placed inside a heated enclosure with accompanying electrical connections for the ESI current.

FIG. 4 is a schematic drawing of another embodiment of the invention where multiple LC columns are placed inside a heated enclosure with accompanying electrical connections for the ESI current. Element 20 represents a first LC column. Element 15 represents a union for fluidic connection. Element 5 represents a second LC column. Element 6 represents a micro-tee or micro-cross for direct application of LC gradient to run LC separation and for applying electrical potential to the liquid inside the columns. Element 14 represents a conductor inserted into micro-tee micro-cross 6 serving for application of high voltage to liquid inside the column to create the electrospray at the ESI tip 9. In this embodiment, the first and second LC columns including the ESI tip 9 are maintained in a thermo-stabilized region.

In one embodiment, the measured temperature serves in a temperature control feedback loop of a power unit responsible for heating the gas flow 13 to achieve the necessary temperature of the exposed part of the integrated column. By adjusting electrical power for heating the volume inside the enclosure 1 and by varying temperature or flow rate of a gas 13 blowing in a direction of the exposed part of the integrated column, the entire column temperature can be maintained at nearly the same temperature in this embodiment.

In another embodiment, the enclosure opening can have gas flow 13 toward the ESI tip 9 that is provided by a reduced gas pressure existing near the inlet to the mass spectrometer and an air-tight connection of the interface to the inlet of the mass spectrometer. The resulting pressure gradient would deliver the directed flow.

In one embodiment, a specified length of the integrated column which ends with the ESI tip can be kept at sub atmospheric conditions, thus facilitating suction of the droplets emitted by the ESI tip by the inlet of mass spectrometer (MS) or ion mobility spectrometer (IMS). The pressure difference between the gas in the enclosure and a gas surrounding the ESI tip improves the gas flow from the temperature controlled enclosure or external temperature controlled gas supplying system towards the end of the column with the ESI tip.

Figure 5:
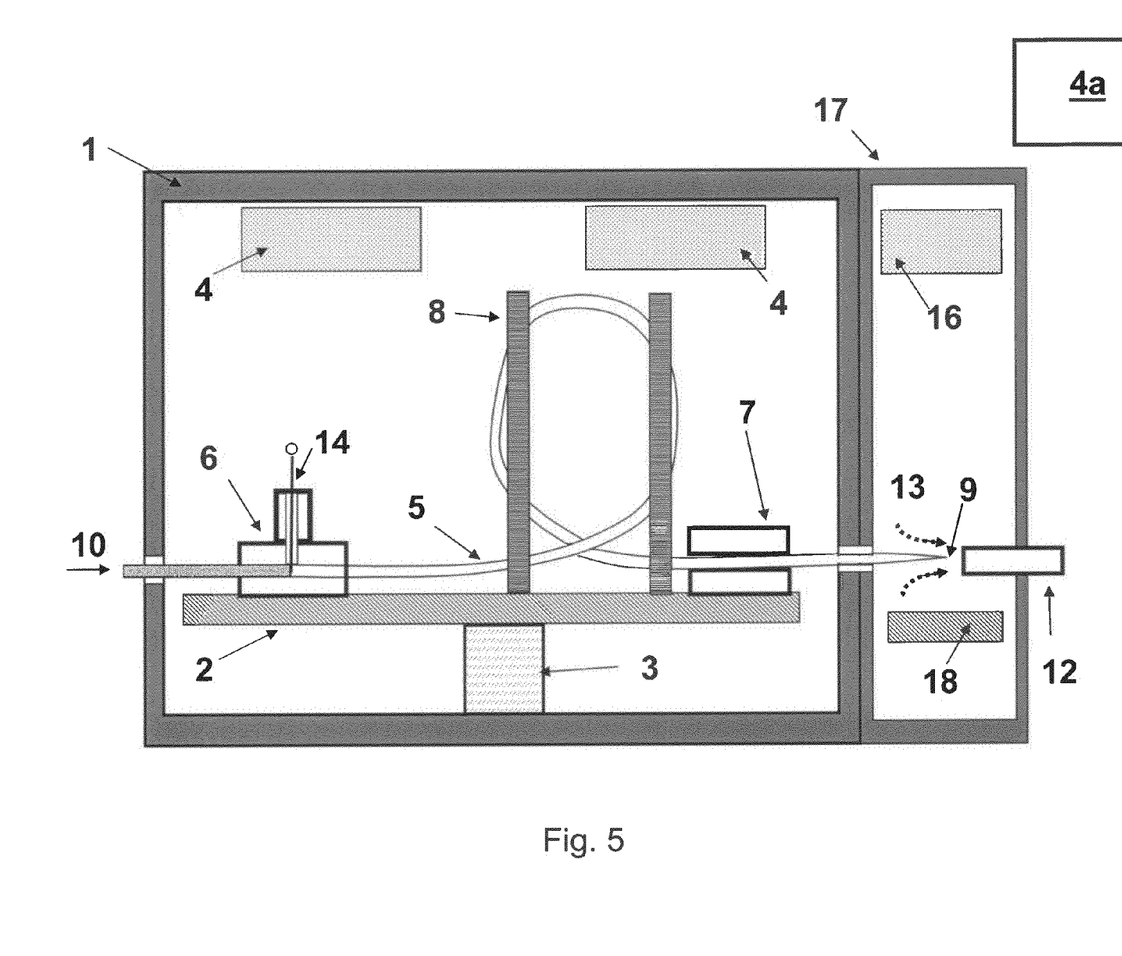
FIG. 5 is a schematic drawing of a nano-LC column placed inside a heated enclosure connected to another enclosure housing the inlet to the mass spectrometer.

In another embodiment, the flow of heated gas from the heated enclosure toward the ESI tip is provided by a reduced gas pressure typically existing near the inlet to the mass spectrometer. To increase the gas flow using the air suction from the MS inlet, at least partially sealed interface of the nano-LC/ESI tip enclosure to an inlet to the mass spectrometer located near the ESI tip is used, as shown in FIG. 5. More specifically, FIG. 5 is a schematic drawing of a nano-LC column placed inside a heated enclosure with heating of the exposed section of the nano-LC/ESI assembly provided by air from the enclosure 1 flowing into enclosure 17 due to the reduced gas pressure existing near the inlet to the mass spectrometer 12 due to the air suction provided by the inlet to MS or IMS. The partially sealed interface of the nano-LC/ESI tip enclosure to the inlet to the mass spectrometer, in one embodiment, can include additional heaters 16, 18 to maintain the exposed ESI tip 9 at the enclosure temperature.

Figure 6:
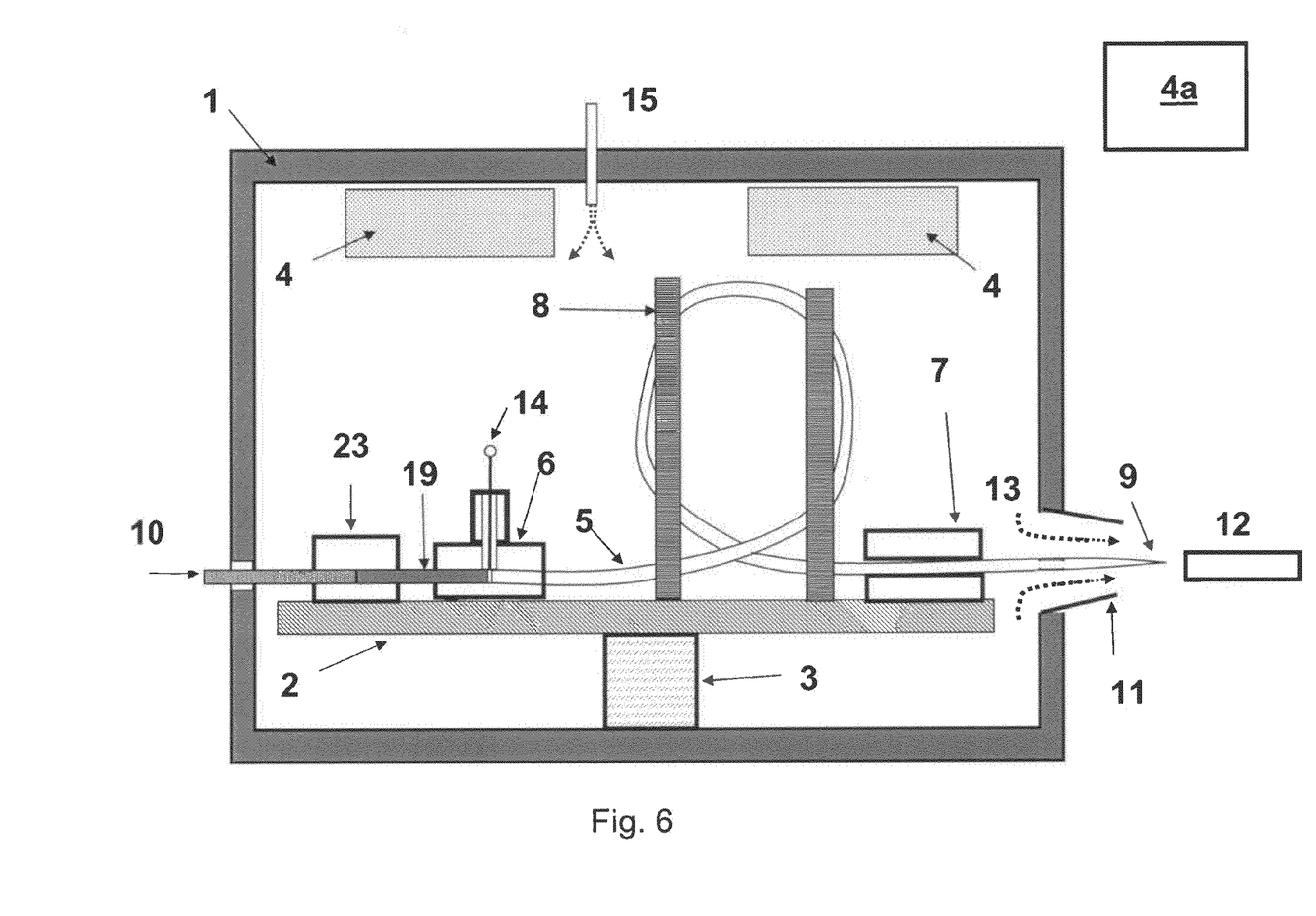
FIG. 6 is a schematic drawing of a precolumn and a nano-LC column placed inside a heated enclosure with the exposed section of the column with the ESI tip heated by blowing the gas heated inside the enclosure toward the ESI tip through the nozzle formed near the opening.

In one embodiment, the integrated column can have a fluid connection to a guarding or trapping precolumn 19, as shown in FIG. 6. More specifically, FIG. 6 is a schematic drawing of precolumn 19 and a integrated nano-LC column 5 placed inside enclosure 1 with the exposed section of integrated column with the ESI tip heated by blowing the gas 13 heated inside the enclosure 1 toward the ESI tip 9 through nozzle 11 formed near the opening in enclosure 1. Fluid connection 23 that can be a union, micro-tee, or micro-cross which function is to connect precolumn 19 to capillary 10 carrying LC gradient, are placed inside the heated enclosure. If a switching valve (not shown) is used for connecting precolumn 19 to the analytical LC column 5, then the switching valve will also be heated by heating elements in enclosure 1 to maintain a uniform temperature along the entire LC system. In another application, the precolumn 19 can be packed with one or several segments of different stationary phases of diverse binding affinity (e.g., titanium oxide, lectins, antibody-based, etc.) for selective enrichment of certain classes of analytes (e.g., phosphopeptides, glycopeptides, antigens, etc.). In such on-line enrichment experiments, a certain species will be expected to pass through the front portion of the column packing (no affinity) and be trapped by the reversed-phase, and eluted when the 1-st LC gradient is applied. In contrast, another species of analytes with high affinity to the enrichment stationary phase will be initially trapped by the front segment of the pre-column, and will stay bound until eluted onto the reversed-phase by sequential injections of specific elution solvents, and then separated during the 2nd LC-MS/MS gradient. In another application where the temperature control is also crucial, the precolumn can be packed with media immobilized reagents to serve as on-line reactors (e.g., tryptic digestion, hydrogen-deuterium exchange, and other).

In one embodiment, a multidimensional LC system which incorporates as the final LC dimension the integrated LC/ESI column is placed into a temperature-controlled enclosure. Similar to previous embodiments, the integrated column end capped with the ESI tip is exposed from the enclosure. In a variant of multidimensional LC called two-dimensional (2D) LC, the integrated LC/ESI column packed with one type of stationary phase is preceded by an analytical column or pre-column packed with another type of stationary phase or several different types of stationary phases. In one particular embodiment of 2D LC called on-line 2D LC, a sample is first loaded and then separated in the 1-st chromatographic dimension (pre-)column. The first liquid fraction eluting from this column is loaded onto a second chromatographic dimension column, which in this case is the integrated LC/ESI column, and the analytes containing in this fraction are separated in the 2-nd chromatographic dimension using the integrated LC/ESI column. The eluent, from the integrated LC/ESI column is analyzed in real time by mass spectrometer or ion mobility spectrometer. Then, after the chromatographic separation in the 2-nd dimension is completed, the second fraction from the 1-st dimension column is loaded onto the 2-nd dimension column (i.e., integrated LC/ESI column). Again, the analytes are separated in and eluting from the integrated LC/ESI column, and analyzed in real time by mass spectrometer or ion mobility spectrometer. In this way, fractions eluting from the column representing 1-st dimension are loaded one by one onto the integrated column representing the 2-nd dimension, then chromatographically separated in the integrated column, electrosprayed from the ESI tip of the integrated column, and detected using mass spectrometer or other means of chemical analysis.

In another multidimentional LC-MS application, several stationary phases can be packed within the same capillary of the LC column or the same precolumn.

In one embodiment of the invention, the precolumn 19 provides a guarding functions for the analytical column 5 preventing its contamination. Fluid connection 23 that can be a union or micro-Tee provides delivery of electrical current to the liquid inside the column to perform the electrospray ionization at the ESI tip. Accordingly, there is a power supply for providing generally stable electrical voltage to the fluid inside the integrated column.

In another embodiment, the heater assembly 4 can include several independently controlled heaters where each element can also include a temperature sensor. The temperature distribution in the enclosure 1 can be varied (or compensated for) by passing different power through different heaters and monitoring the temperature in several points inside the enclosure. In another embodiment, the temperature sensors providing information on temperature distribution can be integrated with the column and coupled to a temperature controller.

In one embodiment, the temperature uniformity along the column would be +/−2° C. In another embodiment, the temperature uniformity along the column would be +/−1° C. In another embodiment, the temperature uniformity along the column would be +/−0.1° C.

One embodiment of the invention includes one or several air steering devices or fans that provide forced air circulation both inside the enclosure and near exposed part of the column 5 including the ESI tip 9.

In one embodiment of the invention, a homogeneous temperature distribution is maintained along integrated capillary column including liquid chromatography separation columns of different lengths (e.g., from several centimeters to several meters) fixed in enclosure by coiling the LC column and using limiting brackets or other means.

Accordingly, the entire integrated nano-LC/ESI tip assembly that, due to its coiling can be of different lengths, is kept at one and the same elevated temperature. One feature of the design is that the central section of the nano-LC column, the section of the nano-LC column that is inserted into a union (micro-Tee), the section of the nano-LC column that forms the ESI tip, as well as the section of the HPLC capillary delivering liquid flow into the nano-LC column are kept at the same elevated temperature providing better reproducibility of retention times (as illustrated by the data shown in FIG. 7), more narrow elution peaks (see FIG. 8), as well as elimination of peak tailing and an increase in peak intensity (see FIG. 9).

Figure 7:
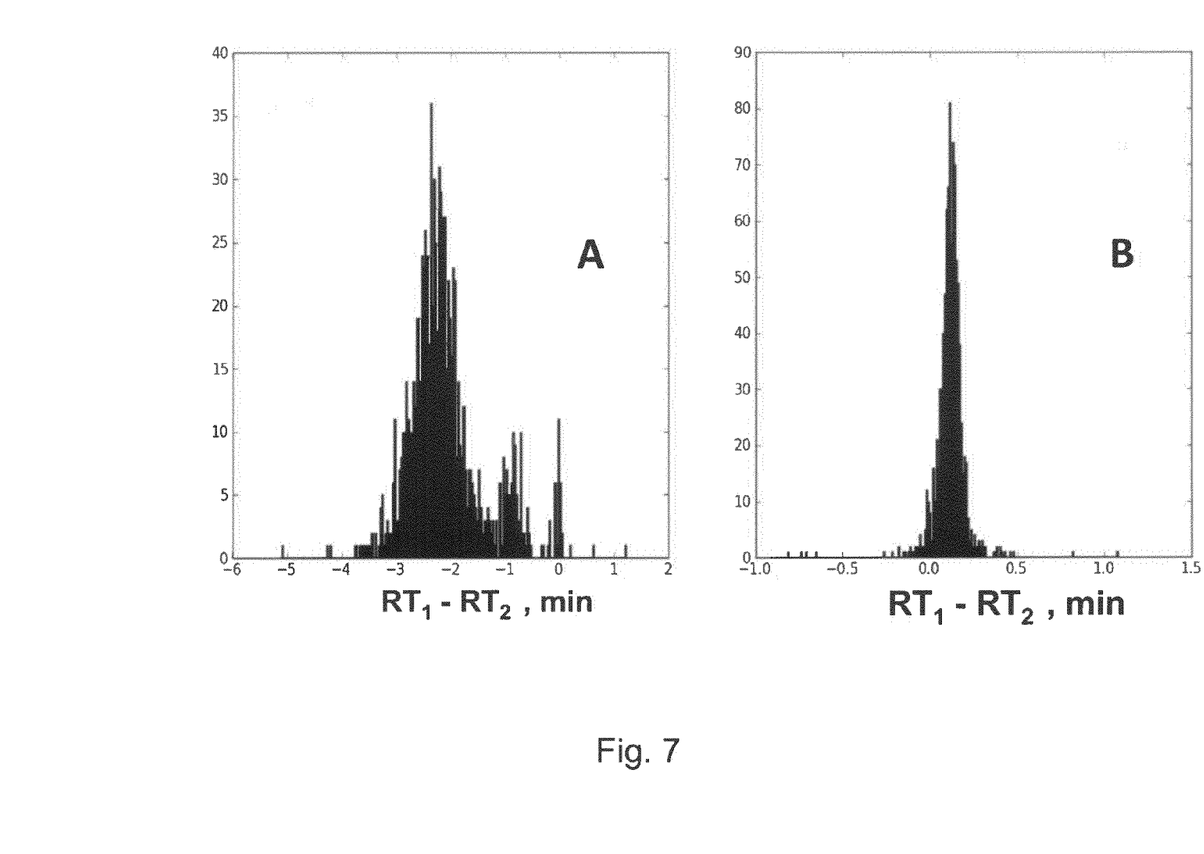
FIG. 7 is an illustration of the improvement in a stability of retention times of peptides separated in reversed-phase nano-LC system at an elevated temperature.

More specifically, FIG. 7 is an illustration of the improvement in a stability of retention times of peptides separated in reversed-phase nano-LC system at an elevated temperature. LC separations have been performed at two different temperatures using homogenously heated nano-LC column. Retention times $RT_1$ (run 1) and $RT_2$ (run 2) of several hundred known peptides were measured in two consecutive LC-MS runs performed at given stable temperature of the column (the eluting peptides were identified based on their MS/MS spectra). Panel A shows the difference in retention times of the same peptides between run 1 and run 2 for 19° C. column temperature. Panel B shows the difference in retention times of the same peptides between run 1 and run 2 for 63° C. column temperature.

Figure 8:
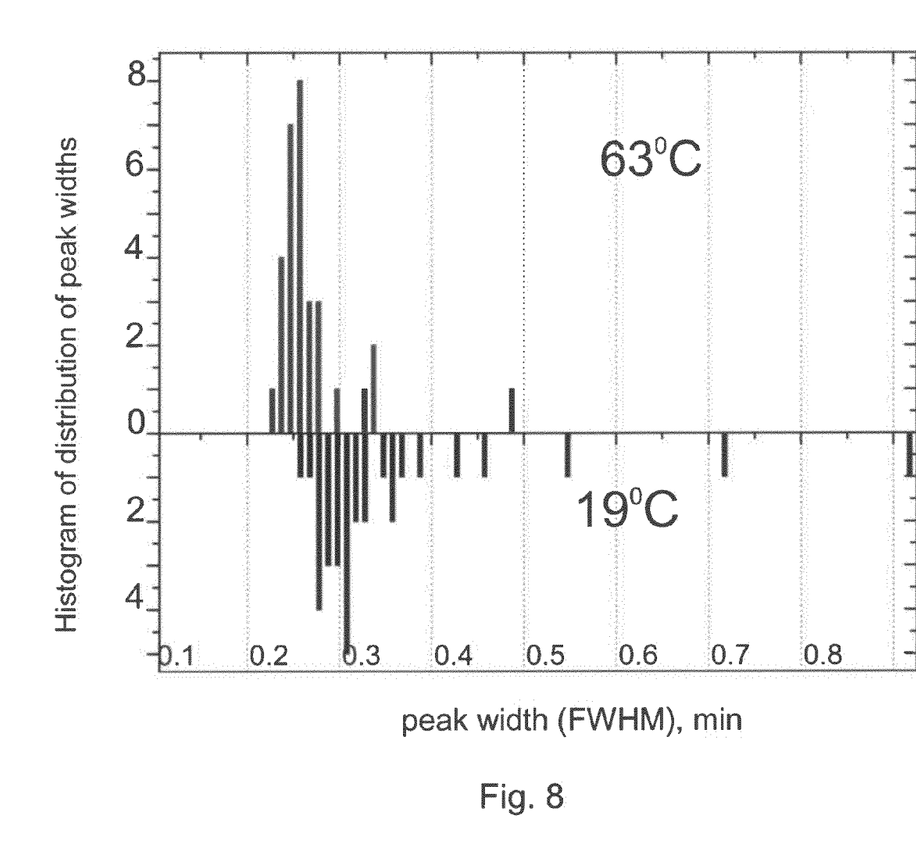
FIG. 8 is an illustration of the reduction of width of chromatographic peaks in reversed-phase nano-LC separation (full width at half maximum—FWHM) at an elevated temperature for 42 known peptides.

FIG. 8 is an illustration of the reduction of width of chromatographic peaks in reversed-phase nano-LC separation (full width at half maximum—FWHM) at an elevated temperature for 42 known peptides. Histograms of peak width distribution are shown for two column temperatures: 19° C. and 63° C.

Figure 9:
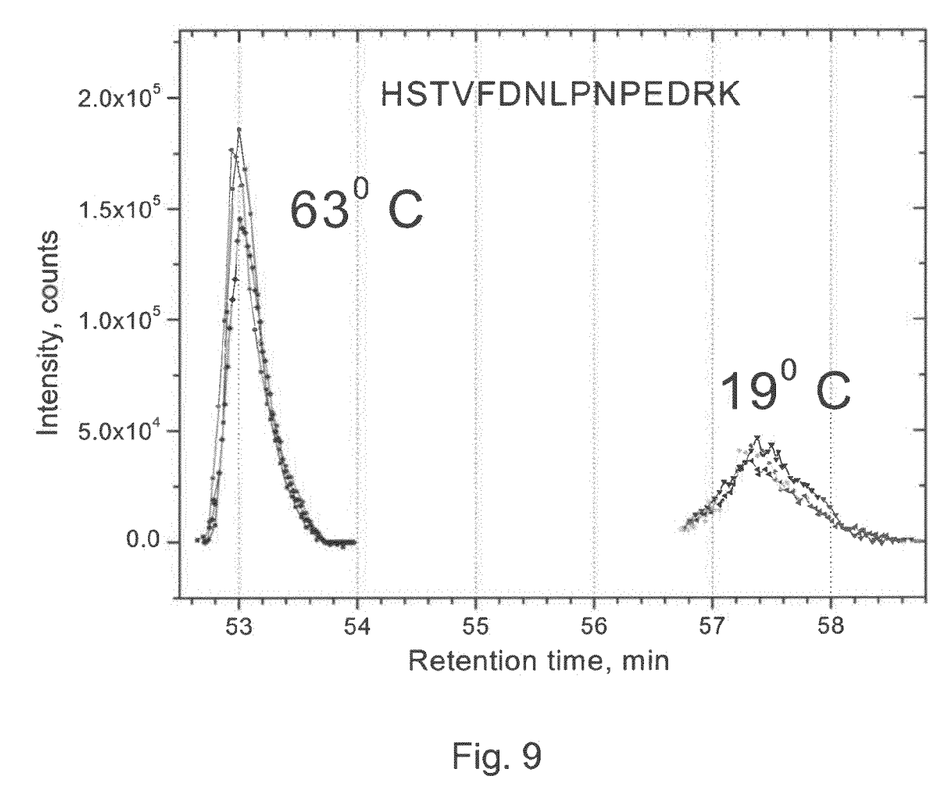
FIG. 9 is an illustration of the effect of elevated temperature on peak width, peak tailing, and peak intensity in the reversed-phase nano-LC separation.

FIG. 9 is an illustration of the effect of elevated temperature on peak width, peak tailing, and peak intensity in the reversed-phase nano-LC separation. Shown are extracted ion chromatograms obtained from six (6) nano-LC separations of peptide HSTVFDNLPNPEDRK performed using homogeneously heated nano-LC column kept at 63° C. (group of 3 peaks on the left) and at 19° C. (group of 3 peaks on the right). Note the reduction in elution windows (FWHMs) provided by the thermostabilized interface.

This invention thus advantageously provides better thermal management for liquid chromatographic separations performed with capillary or nano-LC columns integrated with the ESI tips.

The embodiments discussed herein are illustrative of the present invention. Various modifications or adaptations of the methods and/or specific structures described may become apparent to those skilled in the art. As one example (but not limiting one), the temperature of the LC column can be actively cooled instead of being actively heated (the cooling may be advantageous for separating small molecules). Also, any liquid separation technique can be used instead of liquid chromatography (for example, capillary electrophoresis, capillary electrochromatography, capillary chromatofocusing, monolithic capillary separation techniques, or planar open tubular (PLOT) chromatographic techniques). As one more such example, the same heated enclosure can include more than one LC column.

In one embodiment, regardless of the heating and cooling configurations described above, the temperature of the columns (e.g., 5, 19, and/or 20) integrated into the enclosure 1 can be controllable ramped. The temperature controllable ramp (for example controlled by processor 4a) can provide a method for the separation of analytes in elution time in a liquid chromatography separation column. The method provides a thermo-stabilized volume of substantially the same instant temperature from the entrance of the liquid chromatography separation column to the outlet of an electrospray ionization (ESI) tip. In this method, the heating system of the entire column provides a temperature ramp during some long time interval (from minutes to hours) in such a way that the instant temperature of the entire column is a function of time, but the variation of the instant temperature along the integrated column length is small at any given time.

In one embodiment of the invention, a temperature ramp can serve as a substitute for a conventional acetonitrile gradient ramp (run).

For example, compounds collected for the LC-MS analysis are frequently collected in solutions comprising water mixed with a small percent of acetonitrile or methanol. In LC separation, the compounds are forced by a liquid (the mobile phase) to run through a column that is packed with a stationary (i.e., immobile) phase composed of irregularly or spherically shaped particles, a porous monolithic layer, or a porous membrane. In liquid chromatography (LC) utilizing reversed stationary phase, a chemical compound dissolved in water with very small percent of acetonitrile or methanol is first loaded (absorbed) onto a chromatographic column, then salts or other contaminants are washed from the absorbed compound by running through the column water with very small percent of acetonitrile or methanol, and, in the next step, upon the percent of acetonitrile in water is steadily increasing, the compounds elute from the column towards a mass analyzer (e.g., a mass spectrometer). In this last step, a fraction (%) of acetonitrile or methanol in the mobile phase increases linearly with the time. Some compounds elute from the column when there is a low % of acetonitrile eluting from the column, other compounds elute from the column when there is a high % of acetonitrile eluting from the column. This technique is referred to as liquid chromatographic separation of compounds at gradient conditions and provides a kind of chemical separation before the eluted compounds are introduced to a mass spectrometer.

A gradient LC run utilizing reversed stationary phase typically starts with washing cycle, when one runs through the LC column a "washing solution". Typically, this solution comprises 98% of water and 2% of acetonitrile and washes out salts or other contaminants from the absorbed compounds. Other % of acetonitrile or methanol in washing solution is also possible. Then, in the next phase, that can last from one min to several hours, the percentage of acetonitrile (or methanol) in the mobile phase increases from 2% (or higher %) to 60% (or higher %) in a linear manner. Typically, the percentage of acetonitrile (or methanol) entering the column from the LC system is strictly proportional to the time elapsed from the start of gradient LC run.

In one embodiment of the invention, instead of raising (like in the reversed-phase separation) or decreasing (like in the normal-phase separation) a percentage of acetonitrile over time, the temperature of the entire column can be increased with time (or decreased with time) in linear or non-linear manner while keeping the percentage of acetonitrile over time constant. Under a condition of fixed % of acetonitrile in a solution running through the column, compounds separate at different rates because of the changing temperature.

For some applications of LC-MS analysis this technique provides a discriminator.

In some other embodiment of the invention, raising (or falling) percentage of acetonitrile over time is accompanied by the gradual raise (or fall) of the temperature of the entire column. Compounds in that combined run are separated due to both gradual change in the percentage of acetonitrile in the mobile phase running through the LC column and change in the LC column temperature.

In one embodiment of the invention, processor 4a is programmed with instructions and has circuitry to control the heating elements described above as well as to receive input from sensors monitoring the temperature at various points in enclosure 1. Processor 4a is programmed to ramp and control temperatures in enclosure 1 according to preset algorithms. Processor 4a is programmable to allow a user to set the temperature ramp and/or temperature of enclosure 1.

Accordingly, processor 4a can include a central processing unit (CPU) having a storage medium on which is provided a database of instructions and a database of recorded temperature ramps. Processor 4a can include a bus or other communication mechanism for communicating information to and from itself, or other networked computers by hardwire or wireless communication. Processor 4a can include a main memory, such as a random access memory (RAM) or other dynamic storage device (e.g., dynamic RAM (DRAM), static RAM (SRAM), and synchronous DRAM (SDRAM)), coupled to the bus for storing information and instructions to be executed by processor. In addition, the main memory may be used for storing temporary variables or other intermediate information during the execution of instructions by the processor. Processor 4a can include a read only memory (ROM) or other static storage device (e.g., programmable read only memory (PROM), erasable PROM (EPROM), and electrically erasable PROM (EEPROM)) coupled to the bus for storing static information and instructions for the processor.

Processor 4a can include a disk controller coupled to the bus to control one or more storage devices for storing information and instructions, such as a magnetic hard disk, and a removable media drive. The storage devices may be added to processor 4a can include using an appropriate device interface (e.g., small computer system interface (SCSI), integrated device electronics (IDE), enhanced-IDE (E-IDE), direct memory access (DMA), or ultra-DMA). Processor 4a can include special purpose logic devices (e.g., application specific integrated circuits (ASICs)) or configurable logic devices (e.g., simple programmable logic devices (SPLDs), complex programmable logic devices (CPLDs), and field programmable gate arrays (FPGAs)).

Processor 4a may also include a display controller coupled to the bus to control a display, such as a cathode ray tube (CRT), for displaying information to a computer user. Input devices, such as a keyboard and a pointing device, can be provide for interacting with a computer user and providing information to the processor 4a such that the user as noted above can set the temperature and/or temperature ramp of enclosure 1. One or more processors may be used for processor 4a in a multi-processing arrangement may also be employed to execute the sequences of instructions contained in main memory. In alternative embodiments, hard-wired circuitry may be used in place of or in combination with software instructions. Thus, embodiments are not limited to any specific combination of hardware circuitry and software.

Processor 4a can include at least one computer readable medium or memory for holding instructions programmed according to the teachings of the invention and for containing data structures, tables, records, or other data described herein. Examples of computer readable media are compact discs, hard disks, floppy disks, tape, magneto-optical disks, PROMs (EPROM, EEPROM, flash EPROM), DRAM, SRAM, SDRAM, or any other magnetic medium, compact discs (e.g., CD-ROM), or any other optical medium, punch cards, paper tape, or other physical medium with patterns of holes, a carrier wave (described below), or any other medium from which a computer can read.

Numerous modifications and variations of the invention are possible in light of the above teachings. It is therefore to be understood that within the scope of the appended claims, the invention may be practiced otherwise than as specifically described herein.

The invention claimed is:

1. A liquid chromatography interface system comprising:
   an integrated column/electrospray ionization (ESI) tip assembly including,
   a liquid chromatography separation column,
   an ESI tip for generating ions having at least one emitting channel with an internal size less than or equal to 30 microns, and
   a temperature-controlled enclosure enclosing the liquid chromatography separation column;

said enclosure having at least one opening and said ESI tip exposed outside the enclosure through said at least one opening;

said enclosure having a heating or cooling device providing a substantially homogeneous distribution of temperature throughout an internal space of the enclosure where the liquid chromatography separation column is disposed;

said enclosure including at least one gas flow mixing element to permit heat exchange by directing a flow of gas toward the ESI tip, wherein the integrated column/ESI tip assembly resides within a thermo-stabilized volume of substantially the same temperature from an entrance of the liquid chromatography separation column to an end of the ESI tip.

2. The system of claim 1, wherein said column provides liquid chromatography separation in at least one of the following liquid phase separation modes: reversed-phase, normal phase, hydrophilic interaction liquid chromatography phase (HILIC), capillary electrophoresis, size exclusion, solid phase extraction, capillary electrochromatography, capillary chromatofocusing, capillary isoelectric focusing, multidimentional chromatography, on-line enrichment, monolithic capillary separation technique, planar open tubular (PLOT) chromatographic technique, and electrostatic repulsion liquid chromatography phase (ERLIC).

3. The system of claim 1, wherein said liquid chromatography separation column comprises at least one of a capillary column and a nano-LC column,
said at least one of a capillary column and a nano-LC column having inside diameter from 2 microns to 500 microns.

4. The system of claim 3, wherein said at least one of a capillary column and a nano-LC column has a pulled end used as said ESI tip.

5. The system of claim 3, wherein at least part of said at least one of a capillary column and a nano-LC column comprises a coiled column.

6. The system of claim 5, wherein said coiled column is in a fixed position inside the enclosure.

7. The system of claim 1, further comprising:
a pre-column which adjoins said integrated column/ESI tip assembly using a union member.

8. The system of claim 7, wherein said pre-column is located in said thermo-stabilized volume to have the enclosure temperature.

9. The system of claim 7, wherein said pre-column is held at temperature different from said enclosure temperature.

10. The system of claim 7, further comprising
an ESI voltage source connected to said union member.

11. The system of claim 1, where said ESI tip is exposed outside said enclosure at a distance not exceeding 10 mm from said opening.

12. The system of claim 1 wherein said heater includes at least one temperature controller.

13. The system of claim 1, further comprising:
an analyzer configured to analyze ions from the ESI tip,
wherein said gas flow toward said ESI tip is provided by a reduced gas pressure existing near an inlet to the analyzer.

14. The system of claim 13, further comprising:
a housing interfacing said enclosure to said inlet,
said housing at least partially sealing said enclosure with said inlet of the analyzer.

15. The system of claim 14, further comprising a heater inside said housing.

16. The system of claim 1 wherein said gas flow is directed toward said ESI tip through said at least one opening in the enclosure.

17. The system of claim 1, further comprising:
a mass spectrometer (an MS) with an inlet located near said ESI tip for introduction of said ions inside MS for mass analysis,
wherein said gas flow toward said ESI tip is provided by a reduced gas pressure existing near the inlet to the mass spectrometer.

18. The system according to claim 1, wherein said gas flow is supplied from an additional source of temperature controlled gas.

19. The system of claim 1, further comprising:
a gas flow heating element that maintains said gas flow temperature at the enclosure temperature.

20. The system of claim 1 wherein said liquid chromatography separation column is coiled inside said enclosure, for use of columns of different lengths.

21. The system of claim 1, wherein said temperature-controlled enclosure is temperature controlled to ramp over time a temperature of said integrated column.

22. A liquid chromatography interface comprising:
an integrated column/electrospray ionization (ESI) tip assembly including,
a liquid chromatography separation column,
an ESI tip for generating ions, and
a temperature-controlled enclosure enclosing the liquid chromatography separation column;
said enclosure having at least one opening and said ESI tip exposed outside the enclosure through said at least one opening;
said enclosure having a heating or cooling device providing a substantially homogeneous distribution of temperature throughout an internal space of the enclosure where the liquid chromatography separation column is disposed;
said enclosure holding liquid chromatography separation columns having different lengths,
wherein the integrated column/ESI tip assembly, including the liquid chromatography separation columns having different lengths, resides within a thermo-stabilized volume of substantially the same temperature from an entrance of the liquid chromatography separation column to an end of the ESI tip.

23. A liquid chromatography interface comprising:
a liquid chromatography separation column,
a temperature-controlled enclosure enclosing the liquid chromatography separation column;
said enclosure having a heating or cooling device providing a substantially homogeneous distribution of temperature throughout an internal space of the enclosure where the liquid chromatography separation column is disposed to provide a thermo-stabilized volume of substantially the same temperature from an entrance of the liquid chromatography separation column to an end of the liquid chromatography separation column,
wherein the substantially homogeneous enclosure temperature distribution has a temperature differential from the entrance of the liquid chromatography separation column to the end of the liquid chromatography separation column of less than +/−2° C.

24. A method for separation of analytes in elution time in a liquid chromatography separation column, comprising:

providing a thermo-stabilized volume of substantially the same temperature from an entrance of the liquid chromatography separation column to the end of an electrospray ionization (ESI) tip;

transiting a sample through the liquid chromatography separation column to the end of the ESI tip.

25. The method of claim 24, wherein providing comprises:
maintaining a temperature differential from the entrance of the liquid chromatography separation column to the ESI tip of less than +/−2° C.

26. The method of claim 24, wherein providing comprises:
maintaining a temperature differential from the entrance of the liquid chromatography separation column to the ESI tip of less than +/−1° C.

27. The method of claim 24, wherein providing comprises:
maintaining a temperature differential from the entrance of the liquid chromatography separation column to the ESI tip of less than +/−0.1° C.

28. The method of claim 24, wherein transiting comprises:
eluting a single analyte species from the ESI tip within a time frame range of 1-600 minutes.

29. The method of claim 24, further comprising:
analyzing eluents from an integrated column/ESI tip assembly by one of mass spectrometry, ion mobility spectrometry, and light scattering.

30. A system for analyte characterization, comprising:
an integrated column/ESI tip assembly including,
a liquid chromatography separation column,
an ESI tip for generating ions, a temperature-controlled enclosure surrounding the liquid chromatography separation column, and
a mechanism configured to characterize an analyte eluting from the liquid chromatography separation column;
said enclosure having at least one opening and the ESI tip is exposed outside the enclosure through the opening;
said enclosure having a heating or cooling device providing a substantially homogeneous distribution of temperature throughout an internal space of the enclosure where the liquid chromatography separation column is disposed; and
said enclosure including at least one gas flow mixing element to permit heat exchange by directing a flow of gas toward the ESI tip,
wherein the integrated column/ESI tip assembly resides within a thermo-stabilized volume of substantially the same temperature from an entrance of the liquid chromatography separation column to an end of the ESI tip.

31. The system of claim 30, wherein the mechanism configured to characterize an analyte eluting from the liquid chromatography separation column comprises at least one of mass spectrometer, an ion mobility spectrometer, and a light scattering detector.

32. A system for analyte characterization, comprising:
an integrated column/ESI tip assembly including,
a liquid chromatography separation column,
an ESI tip for generating ions, a temperature-controlled enclosure surrounding the liquid chromatography separation column, and
a mechanism configured to characterize an analyte eluting from the liquid chromatography separation column;
said enclosure having at least one opening and the ESI tip is exposed outside the enclosure through the opening;
said enclosure having a heating or cooling device providing a substantially homogeneous distribution of temperature throughout an internal space of the enclosure where the liquid chromatography separation column is disposed; and
said enclosure holding liquid chromatography separation columns having different lengths,
wherein the integrated column/ESI tip assembly resides within a thermo-stabilized volume of substantially the same temperature from an entrance of the liquid chromatography separation column to an end of the ESI tip.

33. The system of claim 32, wherein the mechanism configured to characterize an analyte eluting from the liquid chromatography separation column comprises at least one of mass spectrometer, an ion mobility spectrometer, and a light scattering detector.

34. A method for separation of analytes in elution time in a liquid chromatography separation column, comprising:
providing a thermo-stabilized volume having a substantially same instantaneous temperature from an entrance of the liquid chromatography separation column to an outlet of an electrospray ionization (ESI) tip;
introducing the analytes into the liquid chromatography separation column in the thermo-stabilized volume;
temperature ramping the substantially same instantaneous temperature of the thermo-stabilized volume over a prescribed duration such that the instantaneous temperature is a controlled as a function of time, with no substantial variation of the instantaneous temperature along a column length; and
eluting the analytes from the ESI tip over said prescribed duration.

35. The method of claim 34, wherein ramping the substantially same instantaneous temperature of the thermo-stabilized volume comprises ramping the instantaneous temperature in a manner in which a percentage of the solvent eluted from the ESI tip remains constant.

* * * * *